Feb. 16, 1971 R. CLEM Plant Pat. 3,026
LIGUSTRUM PLANT
Filed July 30, 1968
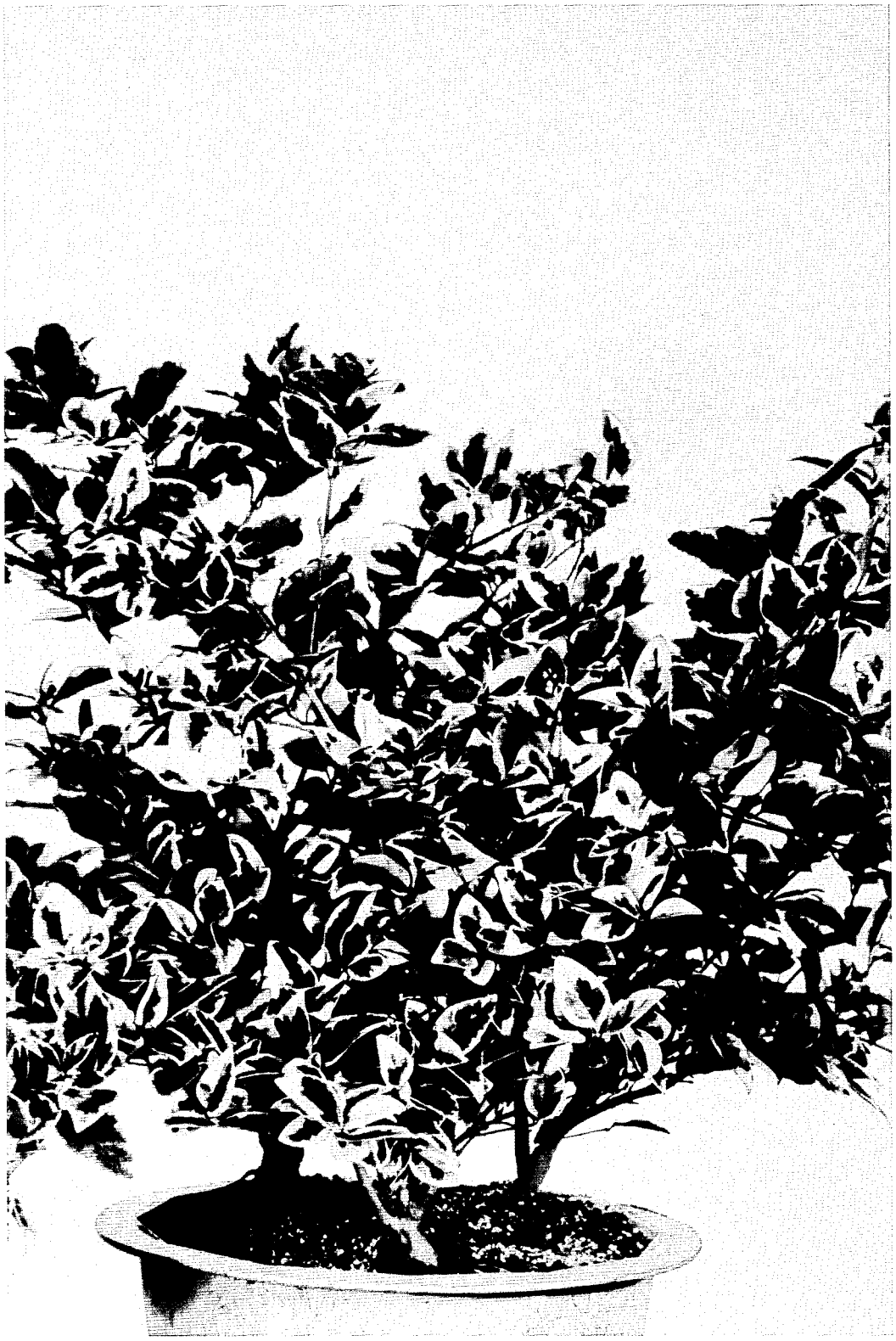

United States Patent Office

Plant Pat. 3,026
Patented Feb. 16, 1971

3,026
LIGUSTRUM PLANT

Richard Clem, Rte. 1, Box 470, Lewisville, Tex. 75067

Filed July 30, 1968, Ser. No. 748,882
Int. Cl. A01h 5/00
U.S. Cl. Plt.—54 1 Claim This invention relates to a new variety of *Ligustrum japonicum* which was discovered by me as a sport on an ordinary *L. japonicum*. I have propagated my new variety by cuttings, and the propagations retain the novel characteristics of the parent mutation.

The new variety, which I have named "Silver Tint Waxleaf," is readily distinguished by its generally white leaf margin. The amount of margin is not uniform throughout the plant, as a few leaves are completely white and others exhibit only a washing-out of the normal, dark green color.

The illustration shows the full range of emargination of mature foliage.

Not only is the new variety distinct from the parent species, it is also readily distinguishable from all other variegated varieties of Ligustrum of which I am aware. Except for the novel leaf markings, the plant is similar to its parent.

I claim:

1. A new and distinct variety of *Ligustrum japonicum* characterized by its white leaf margins.

No references cited.

ROBERT E. BAGWILL, Primary Examiner